United States Patent
Allen et al.

(10) Patent No.: US 9,851,327 B2
(45) Date of Patent: Dec. 26, 2017

(54) PHOTOPATTERNABLE GLASS MICRO ELECTROCHEMICAL CELL AND METHOD

(71) Applicant: Maxim Integrated Products, Inc., San Jose, CA (US)

(72) Inventors: Dan G. Allen, Cupertino, CA (US); Anand Chamakura, San Jose, CA (US); Christopher F. Edwards, Sunnyvale, CA (US)

(73) Assignee: Maxim Integrated Products, Inc., San Jose, CA (US)

( * ) Notice: Subject to any disclaimer, the term of this patent is extended or adjusted under 35 U.S.C. 154(b) by 334 days.

(21) Appl. No.: 14/497,730

(22) Filed: Sep. 26, 2014

(65) Prior Publication Data
US 2015/0346138 A1    Dec. 3, 2015

Related U.S. Application Data

(60) Provisional application No. 62/006,299, filed on Jun. 2, 2014.

(51) Int. Cl.
*G01N 27/404*    (2006.01)

(52) U.S. Cl.
CPC ...... *G01N 27/404* (2013.01); *Y10T 29/49149* (2015.01)

(58) Field of Classification Search
CPC .................. G01N 27/28; G01N 27/404; G01N 27/407–27/4078; G01N 27/416
See application file for complete search history.

(56) References Cited

U.S. PATENT DOCUMENTS

| | | | |
|---|---|---|---|
| 8,096,147 B2 | 1/2012 | Flemming et al. | |
| 2004/0137372 A1* | 7/2004 | Livingston | C03C 4/04 430/311 |
| 2010/0183915 A1* | 7/2010 | Tamachi | H01G 9/016 429/185 |
| 2011/0253534 A1* | 10/2011 | Eckhardt | G01N 27/4045 204/417 |
| 2013/0157121 A1* | 6/2013 | Tamachi | H01G 11/04 429/185 |

FOREIGN PATENT DOCUMENTS

JP    2013030750 A  *  2/2013

* cited by examiner

*Primary Examiner* — Louis Rufo
(74) *Attorney, Agent, or Firm* — Advent, LLP

(57) ABSTRACT

A micro electrochemical cell, a micro electrochemical gas sensor, and a method for fabrication of the micro electrochemical cell are described that include a photopatternable glass substrate, two or more embedded electrodes integrated with through-glass vias, and a gas-permeable membrane lid. In an implementation, a micro electrochemical cell includes a photopatternable glass substrate; at least one recess formed in the photopatternable glass substrate; a plurality of through-glass vias formed in the photopatternable glass substrate, at least one electrolyte disposed in the at least one recess; a wicking layer disposed over the at least one electrolyte; and a lid assembly.

15 Claims, 10 Drawing Sheets

PHOTOPATTERNABLE GLASS MICRO ELECTROCHEMICAL CELL AND METHOD

CROSS-REFERENCE TO RELATED APPLICATIONS

The present application claims the benefit under 35 U.S.C. §119(e) of U.S. Provisional Application Ser. No. 62/006,299, filed Jun. 2, 2014, and titled "PHOTOPATTERNABLE GLASS MICRO ELECTROCHEMICAL CELL AND METHOD." U.S. Provisional Application Ser. No. 62/006,299 is herein incorporated by reference in its entirety.

BACKGROUND

An electrochemical cell is a device capable of either deriving electrical energy from chemical reactions or facilitating chemical reactions through the introduction of electrical energy. Electrochemical cells are integral components of electrochemical sensors, which utilize electrodes to produce a current that is related to the amount of a target gas allowing for the measurement of the concentration of the target gas. Electrochemical sensors can be incorporated in devices that measure environmental pollutants, such as carbon monoxide detectors, and may also be used to measure breath alcohol. Because they require very little power to operate, electrochemical sensors have been widely used in personal safety devices that measure toxic gases. Electrochemical cells are also used in manufacturing batteries.

SUMMARY

A micro electrochemical cell, a micro electrochemical gas sensor, and a method for fabrication of the micro electrochemical cell are described that include a photopatternable glass substrate, two or more embedded electrodes monolithically integrated with through-glass vias, and a gas-permeable membrane lid. In an implementation, a micro electrochemical cell that employs example techniques in accordance with the present disclosure includes a substantially planar photopatternable glass substrate having a first side and a second side; at least one recess formed in the first side of the photopatternable glass substrate; a plurality of electrodes formed in the recess in the first side of the photopatternable glass substrate, where the photopatternable glass substrate, the at least one recess, and the plurality of electrodes form a cell body; a plurality of through-glass vias formed in the photopatternable glass substrate, the through-glass vias extending from the first side of the photopatternable glass to the second side of the photopatternable glass, where the plurality of through-glass vias form an electrical connection from the plurality of the electrodes to the second side of the photopatternable glass; at least one electrolyte disposed in the at least one recess; a wicking layer disposed over the at least one electrolyte; and a lid assembly disposed on the cell body and over the at least one recess, the lid assembly including a lid substrate including an aperture, and a porous membrane disposed between the aperture and the at least one recess. In some implementations, a printed circuit board or connector can be coupled with the micro electrochemical cell to form a micro chemical gas sensor. In some embodiments, the micro electrochemical gas sensor includes a micro electrochemical cell and an integrated circuit for biasing electrodes and measuring current. In implementations, one process for fabricating the micro electrochemical cell that employs example techniques in accordance with the present disclosure includes assembling a cell body on a first side of a cell printed circuit board and an integrated circuit device and connector assembly on a second side of the cell printed circuit board; dispensing at least one electrolyte into the cell body; and placing a lid assembly on the cell body.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The detailed description is described with reference to the accompanying figures. The use of the same reference numbers in different instances in the description and the figures may indicate similar or identical items.

DETAILED DESCRIPTION

Overview

Figure 1A:
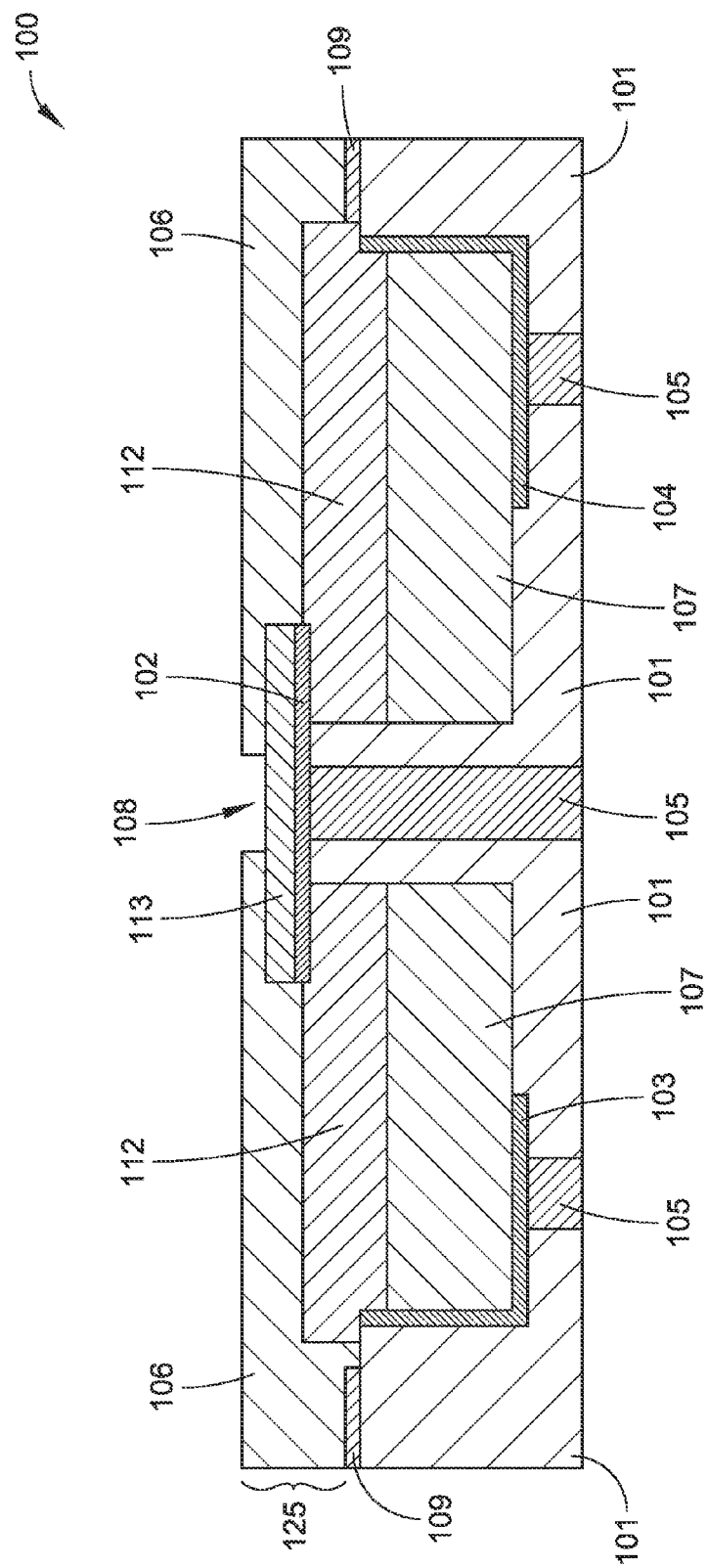
FIG. 1A is a cross section side view illustrating an embodiment of a micro electrochemical cell that includes a photopatternable glass substrate with through-glass vias, and a gas-permeable membrane lid, in accordance with an example implementation of the present disclosure.

An electrochemical cell is a device capable of either deriving electrical energy from chemical reactions or facilitating chemical reactions through the introduction of electrical energy. Electrochemical cells are integral components of electrochemical sensors, which utilize electrodes to produce a current that is related to the amount of a target gas, allowing for the measurement of the concentration of the target gas. Electrochemical sensors can be incorporated in devices that measure environmental pollutants such carbon monoxide detectors, and may also be used to measure breath alcohol. Because they require very little power to operate, electrochemical sensors have been widely used in personal safety devices that measure toxic gases. Electrochemical cells are also used in manufacturing batteries.

Although electrochemical sensors meet the sensitivity and power criteria for sensing gases, difficulty lies in producing sensors that are small enough to be suitable for mobile applications while still maintaining desired robustness, lifetime, and sensitivity needed for air quality monitoring. In particular, the challenges in shrinking electrochemical sensors include maintaining electrode surface area (responsivity), preventing diffusion of analyte to a counter electrode at high concentrations, and maintaining liquid levels in dry climates over extended periods of time. Additionally, for high volume mobile applications, parallel processing, such as wafer-scale or panel-scale processing is also desired. Further, when plastic is used as a substrate for the electrochemical cell, the ability to reduce sidewall thickness and minimize outgassing through the cell walls and joints is limited.

Accordingly, a micro electrochemical cell, an electrochemical gas sensor, and a method for fabrication of the micro electrochemical cell are described that include a photopatternable glass substrate, two or more embedded electrodes monolithically integrated with through-glass vias, and a gas-permeable membrane lid. In an implementation, a micro electrochemical cell that employs example techniques in accordance with the present disclosure includes a substantially planar photopatternable glass substrate having a first side and a second side; at least one recess formed in the first side of the photopatternable glass substrate; a plurality of electrodes formed in the recess in the first side of the photopatternable glass substrate, where the photopatternable glass substrate, the at least one recess, and the plurality of electrodes form a cell body; a plurality of through-glass vias formed in the photopatternable glass substrate, the through-glass vias extending from the first side of the photopatternable glass to the second side of the photopatternable glass, where the plurality of through-glass vias form an electrical connection from the plurality of the electrodes to the second side of the photopatternable glass; at least one electrolyte disposed in the at least one recess; a wicking layer disposed over the at least one electrolyte; and a lid assembly disposed on the cell body and over the at least one recess, the lid assembly including a lid substrate including an aperture, and a porous membrane disposed between the aperture and the at least one recess. In some implementations, a printed circuit board or connector can be coupled with the micro electrochemical cell to form a micro chemical gas sensor. In some embodiments, the micro electrochemical gas sensor includes a micro electrochemical cell and an integrated circuit for biasing electrodes and measuring current. In implementations, one process for fabricating the micro electrochemical cell that employs example techniques in accordance with the present disclosure includes assembling a cell body on a first side of a cell printed circuit board and an integrated circuit device and connector assembly on a second side of the cell printed circuit board; dispensing at least one electrolyte into the cell body; and placing a lid assembly on the cell body.

The disclosed micro electrochemical cell and electrochemical sensor provides better longevity and sensitivity because of etched corrugation or roughness in the glass recess/reservoir, which increases reservoir surface area and sensing area of electrodes. Additionally, the micro electrochemical cell can be small enough to be utilized in mobile devices. Further, the electrochemical cell also provides reduced outgassing and thinner sidewall construction by using a photopatternable glass substrate with low gas permeability. The electrochemical cell is amenable to manufacturing via wafer or panel-scale processing due to decreased size, lithographic feature definition, and enhanced resilience from monolithic construction. The electrochemical sensor can provide a wide sensing spectrum by integrating various kinds of electrochemical cells into a common substrate.

Example Implementations

FIG. 1A illustrates a micro electrochemical cell 100 in accordance with an example implementation of the present disclosure. As shown in FIGS. 1A through 1G, the micro electrochemical cell 100 and a cell body 117 can include a photopatternable glass substrate 101, at least one working electrode 102, at least one reference electrode 103, a counter electrode 104, at least one through-glass via 105, and a lid assembly 125. The cell body 117 can include a photopatternable glass substrate 101 that has been etched to form at least one recess 101A, include at least one through-glass via 105, and/or include at least one electrode 102, 103, 104.

In implementations, a photopatternable glass substrate 101 can include photopatternable or photodefinable glass. Photopatternable or photodefinable glass can include sensitizers that allow unique anisotropic 3D features to be formed through exposure to ultraviolet (UV) light and subsequent baking and etching of ceramic formed after exposure to the UV light. One example of a photodefinable glass includes an alumino-silicate-based glass. In an embodiment, the photopatternable glass substrate 101 includes a photodefinable glass substrate where the glass substrate is optically transparent, chemically inert, and thermally stable (e.g., up to approximately 450° C.). The photopatternable glass substrate 101 can include a glass with a higher coefficient of thermal expansion than a ceramic state. In a specific embodiment, the photopatternable glass substrate 101 is exposed to UV light, baked and converted to ceramic, and etched with an etchant (e.g., HF, etc.) to remove at least a portion of the ceramic. During the light exposure and etching processes, different features can be formed, such as a recess 101A, a hole (e.g., for forming a through-glass via 105), and/or a cavity in the photopatternable glass substrate 101. In implementations, different portions and/or regions of the photopatternable glass substrate 101 can be converted to ceramic and may be etched, re-etched, or left un-etched. In an embodiment, the photopatternable glass substrate 101 can be converted to a ceramic state and left un-etched, for example, to form a light isolation component. The features formed from etching can be filled with other opaque and/or conductive materials, such as an electrode. For example, a conductive through-glass via 105 may be formed by filling a hole etched in the photopatternable glass substrate 101 with a conductive material (e.g., copper).

As illustrated in FIGS. 1A through 1G, the photopatternable glass substrate 101 can include at least one recess 101A formed in the first side of the photopatternable glass substrate 101. In implementations the recess 101A can be formed by lithographically defining, exposing, and annealing the photopatternable glass substrate 101 to create etchable ceramic regions, as disclosed above. In some implementations, the recess 101A can include a contiguous volume configuration (e.g. in other cross sections). The recess 101A can be configured as an electrolyte reservoir for containing a volume of electrolyte 107 and optionally air. In implementations, the electrolyte 107 may be a solid, gel or a liquid.

The cell body 117 and the micro electrochemical cell 100 can include at least one electrode, for example a working electrode 102, a reference electrode 103, and/or a counter electrode 104. An electrode may include an electrical conductor used to make contact with a nonmetallic part (e.g., electrolyte 107, air, etc.) of a circuit (e.g., an electrochemical circuit). In some implementations, the working electrode 102, the reference electrode 103, and/or the counter electrode 104 can include conductive materials (e.g., gold, platinum, etc.). Some specific embodiments of the patterned glass substrate 101 may include only a counter electrode 104 and no reference electrode 103.

In some implementations, the electrodes 102, 103, 104 can be formed using a lithographic process, for instance using a masked metal deposition. Lithographic deposition may provide for the deposition of electrodes that can be as thin as a few hundred nanometers and can permit smaller micro electrochemical cell 100 size using wafer-scale or panel-scale processing while reducing precious metal consumption. Lithographically defining the electrodes can reduce component variation relative to electrodes formed from colloidal inks or dispersions, although these methods may be utilized to fabricate the electrodes 102, 103, 104.

In implementations, the recess 101A can include surface corrugation or serpentine trenches to provide more electrode sensing surface area and to allow for increased dynamic range by better isolating reference electrode 103 and counter electrode 104 from an aperture 108 in a lid assembly 125. Specifically, proximity of the counter electrode 103 or reference electrode 104 to the gas inlet (e.g., the aperture 108) can allow for diffusion of unreacted analyte to the counter electrode 103 and/or reference electrode 104, which reduces cell electrochemical current and/or modifies the cell potential, respectively. Additionally surface roughness in the recess 101A can provide for more electrode surface area.

In some implementations, a shadow mask deposition technique can be employed to isolate electrodes at a second side (e.g., bottom or side distal from the opening of the recess 101A) of a reservoir (e.g., recess 101A). Shadow mask deposition allows for the selective deposition of materials by using micro or nanostencils to cover and precisely define target surfaces. In some embodiments, a stencil can be formed from photopatternable glass. Materials may then be selectively deposited through the shadow mask. In some implementations, a shadow mask technique can be used to isolate the electrodes on the first side of the photopatternable glass substrate.

In some implementations, the micro electrochemical cell 100 can include an adhesion promoting material between metal of the electrode 102, 103, 104 and the photopatternable glass substrate 101. Some examples of an adhesion promoting material can include titanium and/or a thin film.

The combination of the photopatternable glass substrate 101, corrugation in the recess 101A, and monolithic integration can provide for a reduction in size of the micro electrochemical cell 100 to a thickness of less than 2 mm, or even less than 1 mm, and areal dimensions of less than 1 cm×1 cm, or even less than 5 mm×5 mm. In one specific embodiment, a micro electrochemical cell 100 can measure about 3.4 mm×3.4 mm×1.2 mm. The thin side walls of a sturdy material like glass or ceramic formed during formation of a recess 101A allow for a usefully large internal volume of electrolyte 107, which can help improve the lifetime of a micro electrochemical cell 100, especially in dry climates.

Further, the micro electrochemical cell 100 and photopatternable glass substrate 101 can include at least one through-glass via 105, as shown in FIGS. 1A through 1G. A through-glass via can include a vertical hole and/or electrical connection passing through the photopatternable glass substrate 101. In implementations, a through-glass via 105 can extend from a first side (e.g., the side having a recess 101A) of the photopatternable glass substrate 101 to a second side (e.g., side distal from the recess 101A) of the photopatternable glass substrate 101. In other implementations, a through-glass via 105 can be disposed in a side wall of the photopatternable glass 101. The through-glass vias 105 can form an electrical connection from the working electrode 102, reference electrode 103, and/or counter electrode 104 to a connector assembly 120 and/or an integrated circuit device 115 disposed on the second side of the photopatternable glass substrate 101. In implementations, the through-glass vias 105 can be metalized with a conductive material, for example copper, by front side or backside filling. In some embodiments, through-glass vias 105 can be disposed within the recesses and/or located adjacent to the recesses and connected by top metallization. In some implementations, the through-glass vias 105 can be formed by serial etches into the photoexposed and cured photopatternable glass substrate 101. In other implementations, the through-glass via 105 may be laser drilled.

As illustrated in FIGS. 1A through 1G, micro electrochemical cell 100 can include a lid assembly 125. In implementations, the lid assembly 125 further includes a lid 106, an aperture 108 formed in the lid 106, and a porous membrane 113. The lid 106 includes a substantially nonpermeable region, and the aperture 108 includes a gas permeable region. In some implementations, the lid assembly 125 can be formed from a polymer and/or a photodefinable glass. Additionally, the permeable region of the lid assembly 125 can include a porous membrane 113, which can include a gas-permeable material (e.g., polytetrafluoroethylene (PTFE-Teflon), which may additionally include a platinum-based catalyst, such as platinum oxide) or an ion conducting membrane (e.g., Nafion, a sulfonated tetrafluoroethylene based fluoropolymer-copolymer). The lid assembly 125 and lid 106 can include a small aperture 108 through which gas analytes enter the micro electrochemical cell 100. In embodiments, the porous membrane 113 can be disposed adjacent to the aperture 108.

Figure 1B:
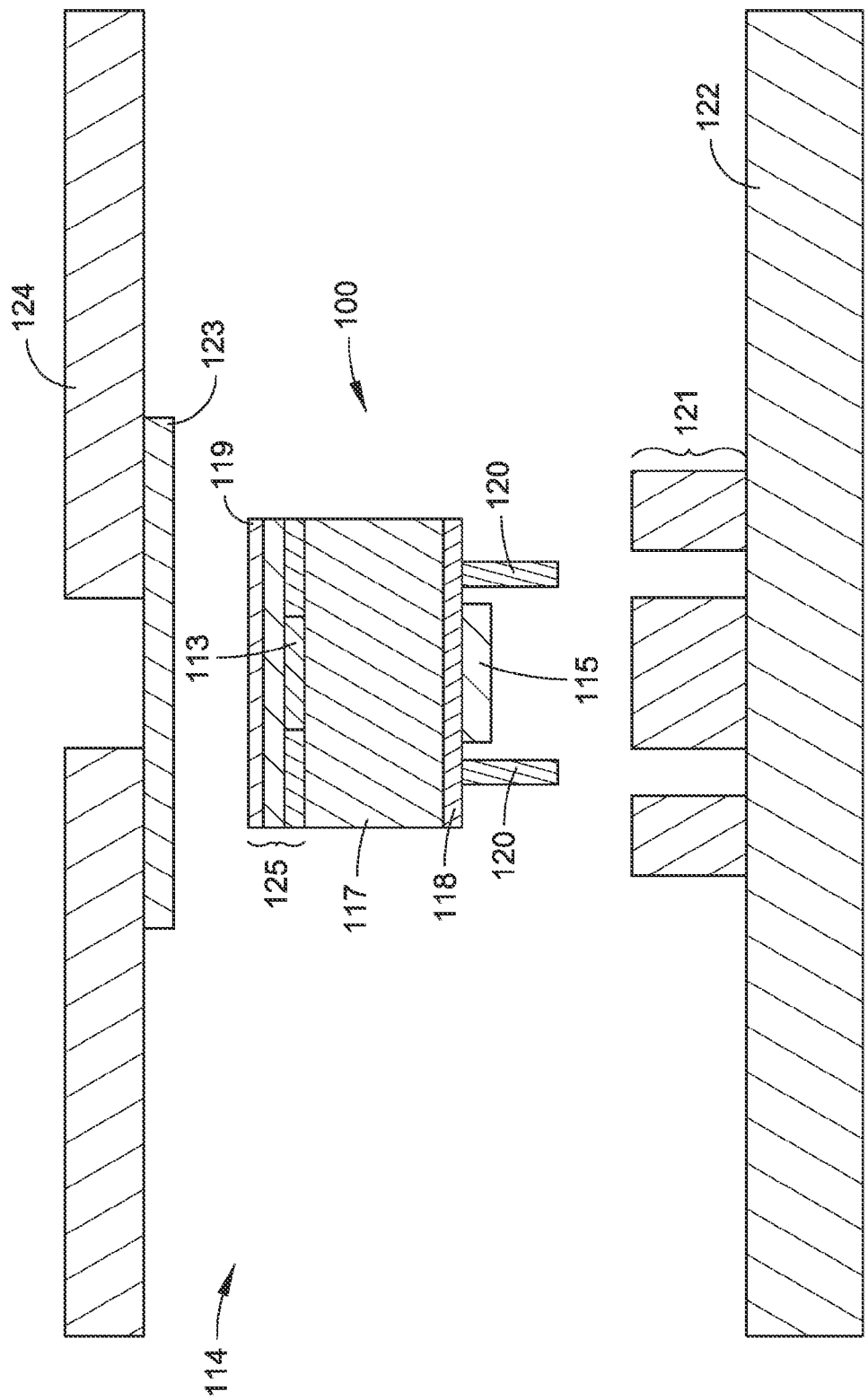
FIG. 1B is a cross section side view illustrating an embodiment of an electrochemical gas sensor that includes a photopatternable glass substrate with through-glass vias, a gas-permeable membrane lid, and an integrated circuit, in accordance with an example implementation of the present disclosure.
Figure 1C:
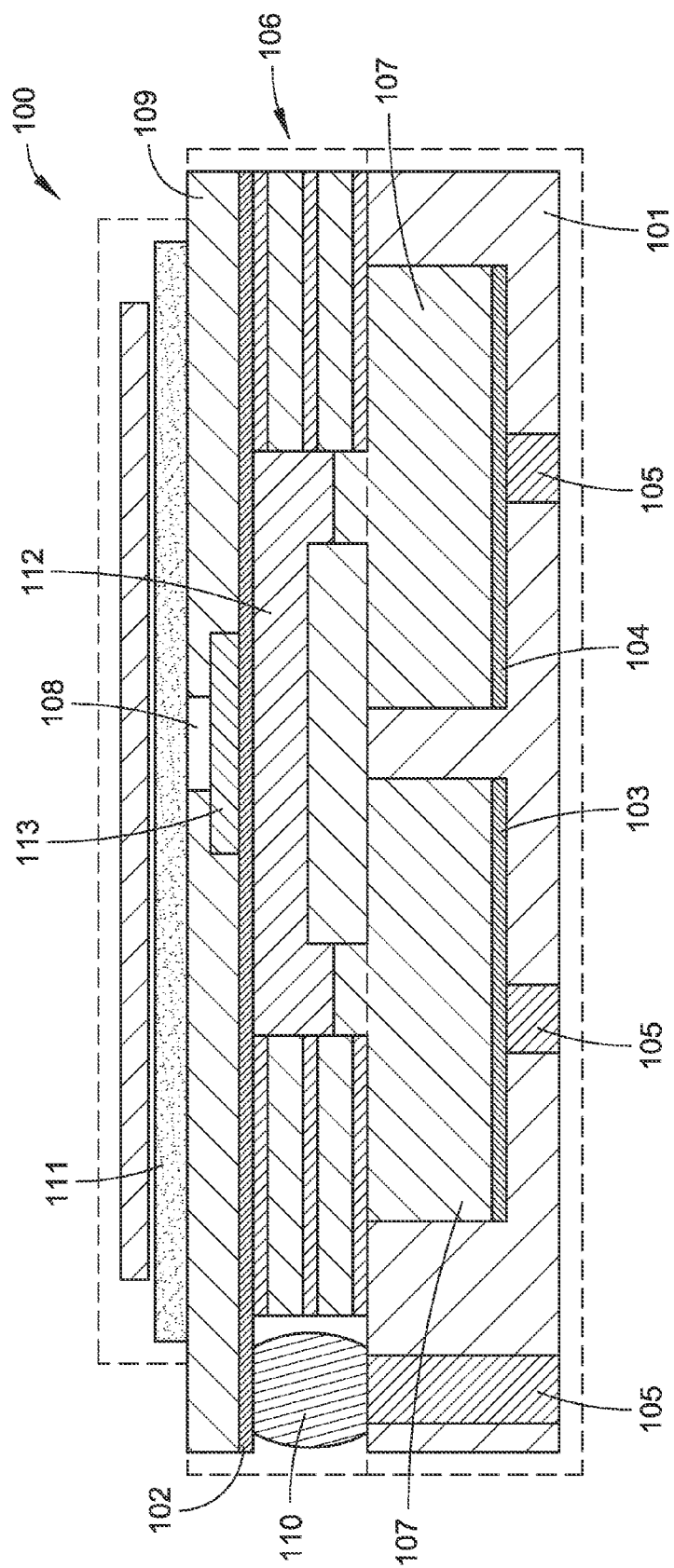
FIG. 1C is a cross section side view illustrating an embodiment of a micro electrochemical cell that includes a photopatternable glass substrate with through-glass vias, and a gas-permeable membrane lid, in accordance with an example implementation of the present disclosure.
Figure 1D:
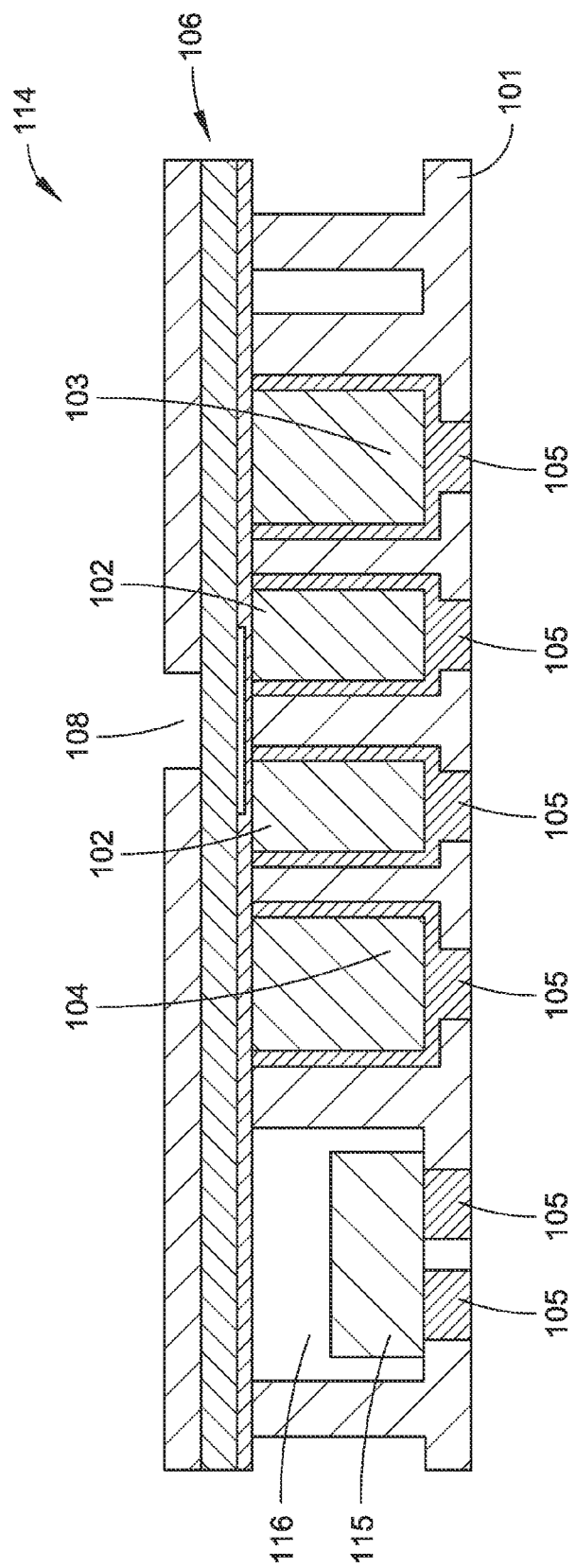
FIG. 1D is a cross section side view illustrating an embodiment of a micro electrochemical cell that includes a photopatternable glass substrate with through-glass vias, and a gas-permeable membrane lid, in accordance with an example implementation of the present disclosure.

As illustrated in FIGS. 1A through 1G, the lid assembly 125 can be placed on and/or coupled to the first side of the cell body 117 and the photopatternable glass substrate 101 with an adhesive 109. In some embodiments, an adhesive 109 with low volatile organic compound content is used because outgassing of the adhesive can cause a time-varying background current in an electrochemical cell, which may affect calibration accuracy. In some specific implementations and as shown in FIG. 1C, an electrical connection between the lid assembly 125 and the photopatternable glass substrate 101 and cell body 117 can include a conductive epoxy 110. In some embodiments, the lid assembly 125 can include a printed chemical filter 111 disposed on the lid 106 and covering the aperture 108. The printed chemical filter 111 can, for example, include a carbon filter with a molecular sieve and a polymer binder or other method of chemical fixation, such as silanation, for stabilization. In a specific example, the filter 11 can include charcoal. In some embodiments, attachment of the lid assembly 125 to the photopatternable glass can be performed subsequent to filling the recess 101A with an electrolyte 107. In other embodiments, the lid assembly 125 may include holes in the porous membrane 113 and/or lid 106 for filling the recess 101A with an electrolyte 107. In these embodiments, the holes in the porous membrane 113 and/or lid 106 can be subsequently sealed.

In some embodiments, the lid assembly 125 can include at least one working electrode 102. In these embodiments, the working electrode 102 can be disposed between the lid 106 and/or the porous membrane 113 and a through-glass via 105. In a specific example, the working electrode 102 can be ink printed using a colloidal ink and/or dispersion onto the lid assembly 125. Additionally, the working electrode 102 can be lithographically defined. In implementations, an electrical connection to a top working electrode 102 can be made using a through-glass via 105 disposed in a post or section of the photopatternable glass 101, as shown in FIG. 1A. In some embodiments, the working electrode 102 may be divided into multiple working electrodes which can be held at different potentials relative to a reference electrode 103. Multiple working electrodes can especially be useful for detecting multiple target analytes (e.g., ethanol, carbon monoxide sulfur dioxide, nitrogen dioxide, ozone, etc.).

In some embodiments, the lid assembly 125 includes a porous material wicking layer 112 between the working electrode 102 and a recess 101A. The wicking layer 112 can provide a triple phase boundary for the working electrode 102 by allowing both air and water to flow through, which results in good sensitivity of the working electrode 102. In a specific example, the wicking layer 112 can include both hydrophillic and hydrophobic properties. In some embodiments, at least one working electrode may be disposed on at least part of the photopatternable glass substrate 101.

FIG. 1B illustrates an electrochemical gas sensor 114 in accordance with an example implementation of the present disclosure. An electrochemical gas sensor 114 can include a micro electrochemical cell 100, an integrated circuit device 115, a connector assembly 120, and/or a printed circuit board 122. In some embodiments, the micro electrochemical cell 100 can include a chip-on-glass configuration for forming the electrochemical gas sensor 114. In a specific embodiment, the photopatternable glass substrate 101 can include an additional recess 116 containing electrical connections (e.g., through-glass via(s) 105) configured to couple to an integrated circuit device 115, but no electrolyte 107. In this embodiment, the integrated circuit device 115 is disposed in the recess 101A. In another embodiment, the integrated circuit device 115 can be disposed on a cell printed circuit board 115. Some examples of an integrated circuit device 115 can include a processor (e.g., an application specific integrated circuit (ASIC)) or another passive device (e.g., a resistor, a capacitor).

In implementations, the electrochemical gas sensor 114 can include a cell printed circuit board 118 and/or a connector assembly 120 coupled to the second side of the micro electrochemical cell 100 and/or photopatternable glass substrate 101. The cell printed circuit board 118 can include a substrate that is configured to mechanically and/or electrically support the electrochemical cell 100, an integrated circuit device 115, and/or a connector assembly 120. A connector assembly 120 can include an electro-mechanical device for joining electrical circuits as an interface using a mechanical assembly. One example of a connector assembly 120 can include a plug and/or socket configured to couple with a corresponding socket or plug, respectively.

In some embodiments, top and bottom redistribution layers can connect electrodes disposed on the first side of the photopatternable glass 101 to an integrated circuit device 115 (e.g., an application specific integrated circuit device) disposed on the second side. In implementations, the integrated circuit device 115 can be used for biasing the electrodes 102, 103, 104 and measuring current. The integrated circuit device 115 can have configurable bias, gain calibration, and/or current nulling calibration. Additionally, the integrated circuit device 115 can provide bi-polar bias and current sensing. In an embodiment, the integrated circuit device 115 can measure an array of cells (e.g., electrolyte 107 in a recess 101A), for example an array of similar cells at different biases for parallel measurement. Further, the integrated circuit device 115 can provide a reference voltage to a reference electrode 103, supply current to a common counter electrode 104, and/or independently bias and measure electrochemical current signal from multiple working electrodes 102. In some implementations, the integrated circuit device 115 can detect if cell impedance is too high or above a predetermined threshold. In some specific embodiments, the integrated circuit device 115 and/or cell printed circuit board 118 can include a temperature sensor. In one particular embodiment shown in FIG. 1D, an electrochemical gas sensor 114 includes an array of monolithic electrochemical cells configured to quasi-independently detect multiple analytes (e.g., CO, NO2, SO2 and O3 or a subset of those chemicals).

Figure 1E:
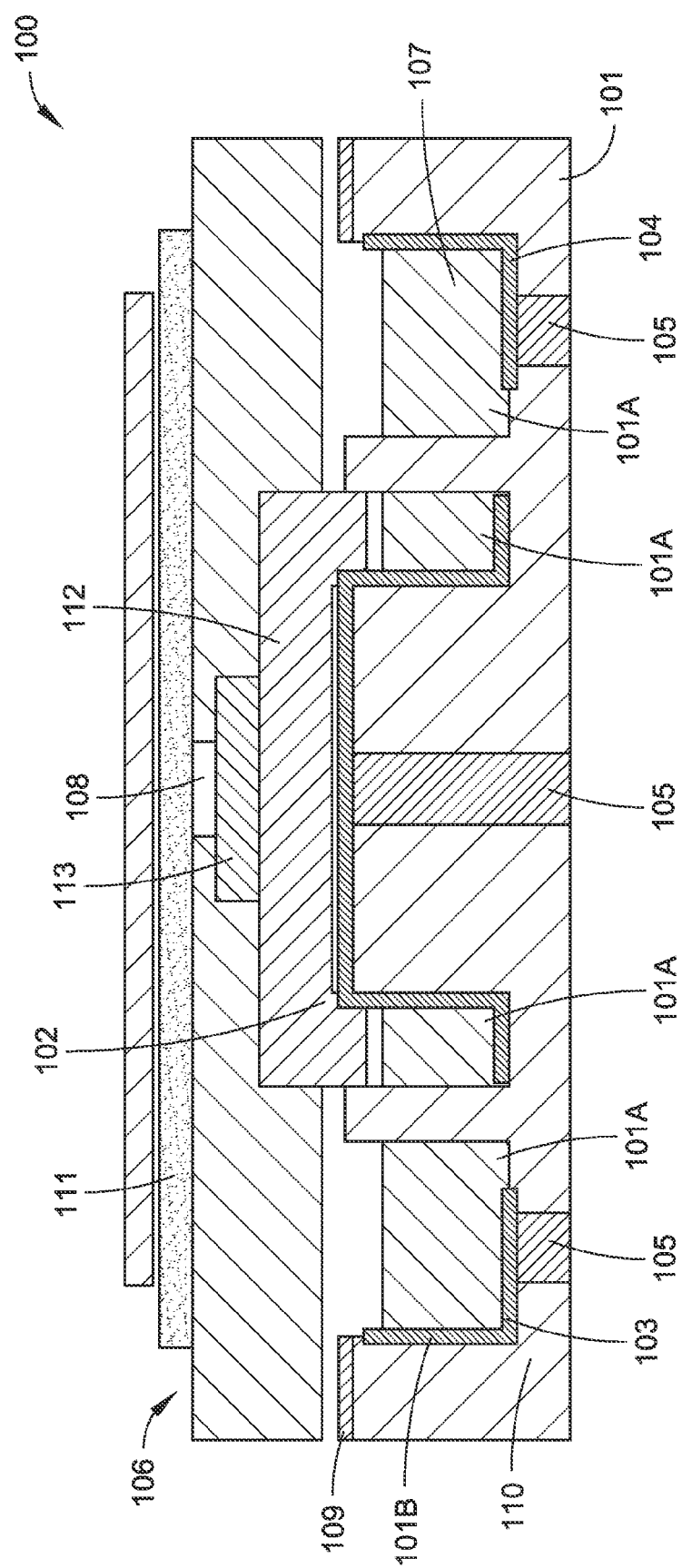
FIG. 1E is a cross section side view illustrating an embodiment of a micro electrochemical cell that includes a photopatternable glass substrate with through-glass vias, and a gas-permeable membrane lid, in accordance with an example implementation of the present disclosure.

FIG. 1E illustrates a micro electrochemical cell 100 in accordance with an example implementation of the present disclosure. This micro electrochemical cell 100 includes at least one working electrode 102 on the photopatternable glass substrate 101. In the embodiment depicted in FIG. 1E, the lid assembly 125 may not include a working electrode. When the working electrode 102 is disposed on the photopatternable glass substrate 101 rather than on the lid assembly 125, the need for a conductive connection between the lid assembly 125 and the photopatternable glass substrate 101 may be eliminated.

Figure 1F:
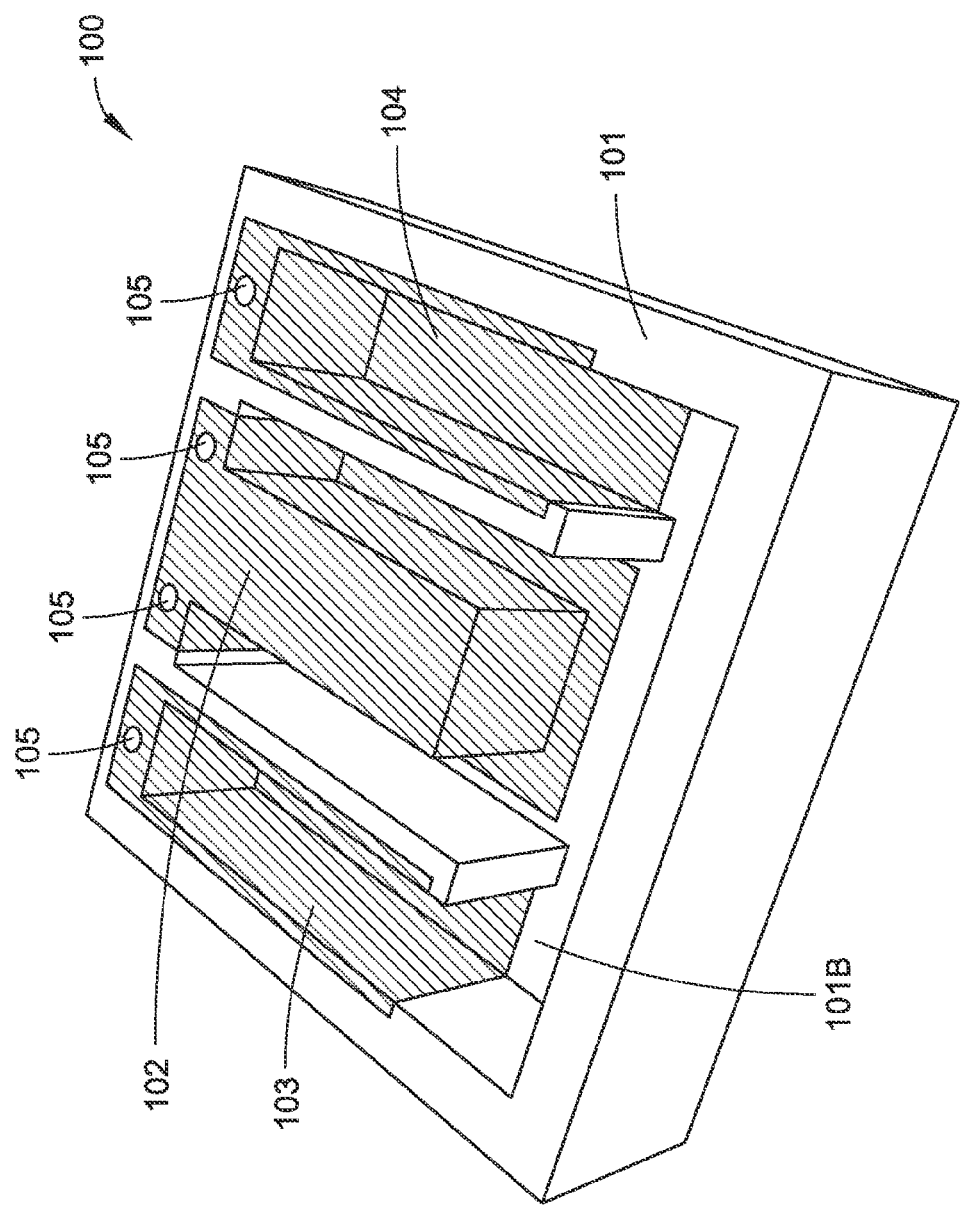
FIG. 1F is an isometric view illustrating an embodiment of a micro electrochemical cell that includes a photopatternable glass substrate with through-glass vias, and a gas-permeable membrane lid, in accordance with an example implementation of the present disclosure.
Figure 1G:
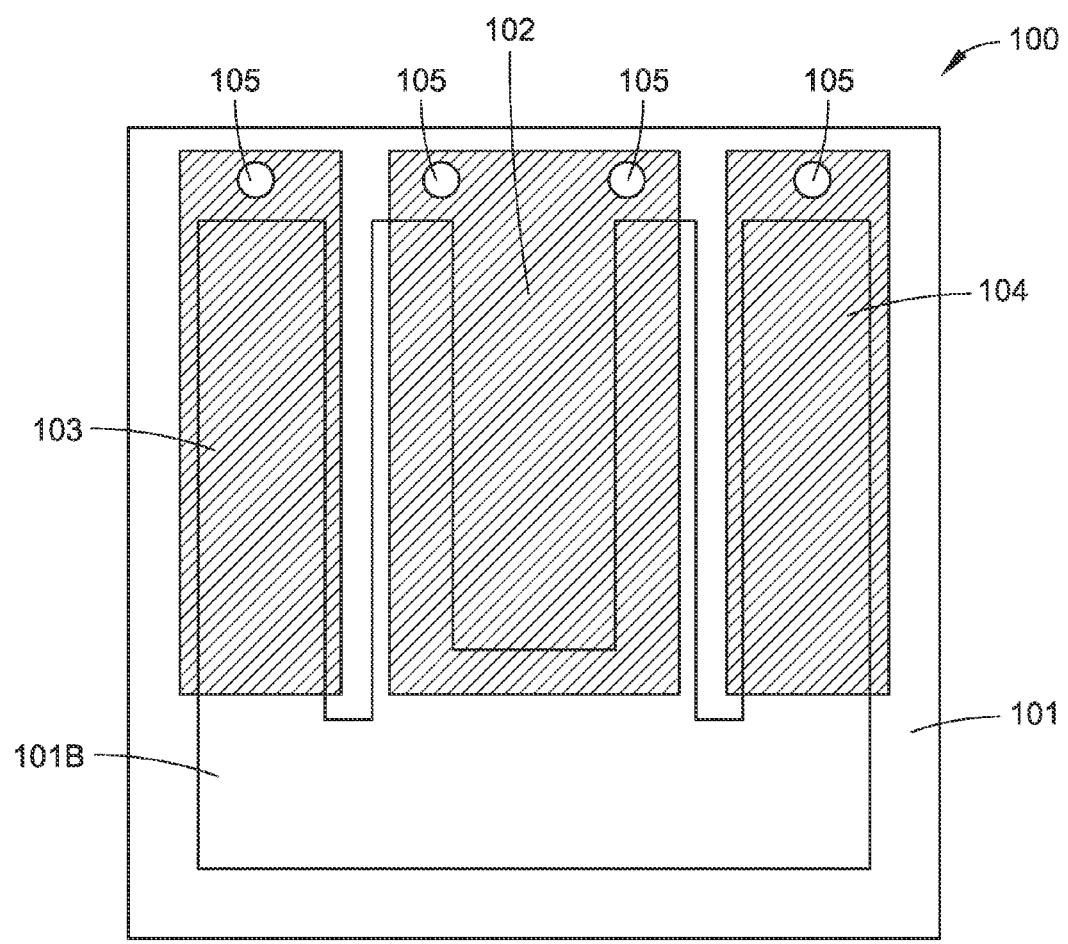
FIG. 1G is a plan view illustrating an embodiment of a micro electrochemical cell that includes a photopatternable glass substrate with through-glass vias, and a gas-permeable membrane lid, in accordance with an example implementation of the present disclosure.

FIG. 1E also illustrates that the side wall regions 101B of the recess 101A in the photopatternable glass substrate 101 can be metalized (e.g., by angled metal deposition) to increase surface area of the electrodes 102, 103, 104. In specific embodiments, the recesses 101A can be connected in a different plane than the cross section shown in FIG. 1E, and the electrolyte 107 can form a contiguous volume. FIG. 1F illustrates an exemplary isometric view of a micro electrochemical cell 100 in accordance with the example implementation illustrated in FIG. 1E. FIG. 1G illustrates a top plan view of a micro electrochemical cell 100 in accordance with the example implementation illustrated in FIGS. 1E and 1F. As shown in FIG. 1F, side through-glass vias 105 may be used in some embodiments. In other embodiments, through-glass vias 105 may be buried under the electrodes at the bottom of the recess. A buried through-glass via 105 configuration may serve to save space relative to through-glass vias 105 located adjacent (e.g., on the sides) of the recess 101A.

Some embodiments of a micro electrochemical cell 100 may include a volatile organic compound absorber. In a specific embodiment, a porous carbon film may be laminated to the lid assembly 125 prior to final micro electrochemical cell 100 assembly. The porous carbon film may include a top barrier layer with apertures that create a tortuous path for gas molecules through the carbon film in order to reach the opening of the porous membrane 113 of the micro electrochemical cell 100 to minimize volatile organic compound cross sensitivity. The porous carbon film may also include a large hole and/or void over a micro electrochemical cell 100 for sensing a volatile organic compound.

In implementations, the micro electrochemical cell 100 and/or the electrochemical sensor 114 can be coupled to a mobile and/or electrical device 124 and/or a printed circuit board 122. Additionally, the micro electrochemical cell 100 can be used as a battery and/or a fuel cell. In some implementations, the micro electrochemical cell 100 and/or the electrochemical sensor 114 and/or device 124 can include environmental protection, such as a water barrier 123.

Example Processes

Figure 2:
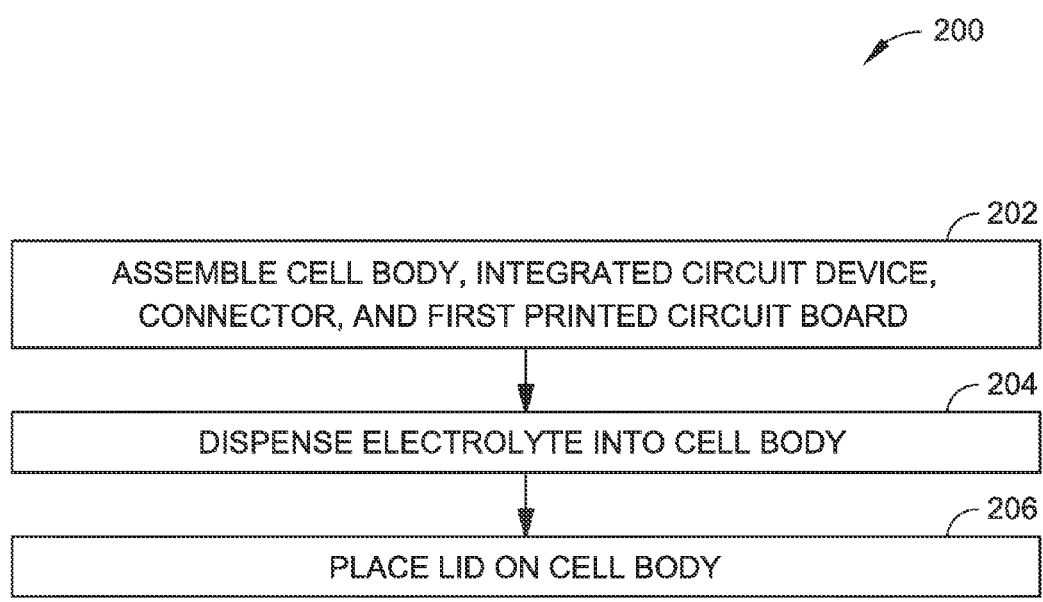
FIG. 2 is a flow diagram illustrating an example process for fabricating a micro electrochemical cell that includes a photopatternable glass substrate with through-glass vias, and a gas-permeable membrane lid, such as the micro electrochemical cell illustrated in FIGS. 1A through 1G.
Figure 3A:
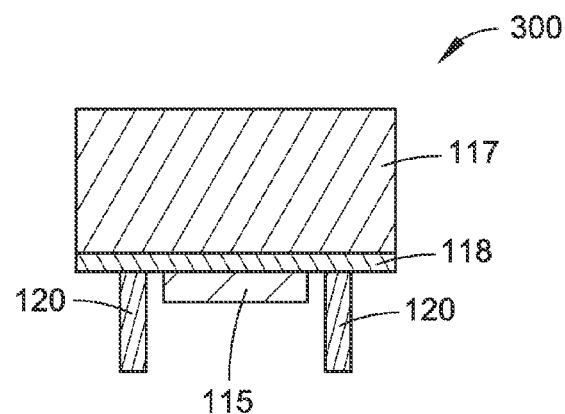
FIG. 3A is a diagrammatic partial cross-sectional side elevation views illustrating the fabrication of a micro electrochemical cell, such as the micro electrochemical cell shown in FIGS. 1A through 1G, in accordance with the process shown in FIG. 2.
Figure 3B:
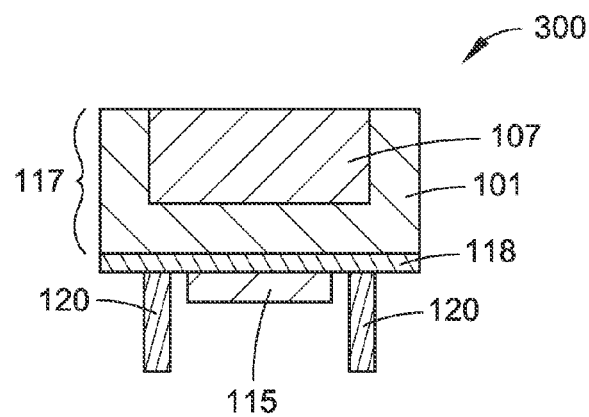
FIG. 3B is a diagrammatic partial cross-sectional side elevation views illustrating the fabrication of a micro electrochemical cell, such as the micro electrochemical cell shown in FIGS. 1A through 1G, in accordance with the process shown in FIG. 2.
Figure 3C:
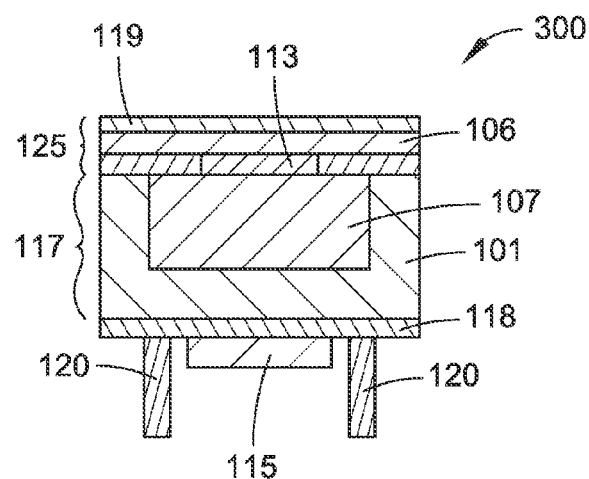
FIG. 3C is a diagrammatic partial cross-sectional side elevation views illustrating the fabrication of a micro electrochemical cell, such as the micro electrochemical cell shown in FIGS. 1A through 1G, in accordance with the process shown in FIG. 2.
Figure 4:
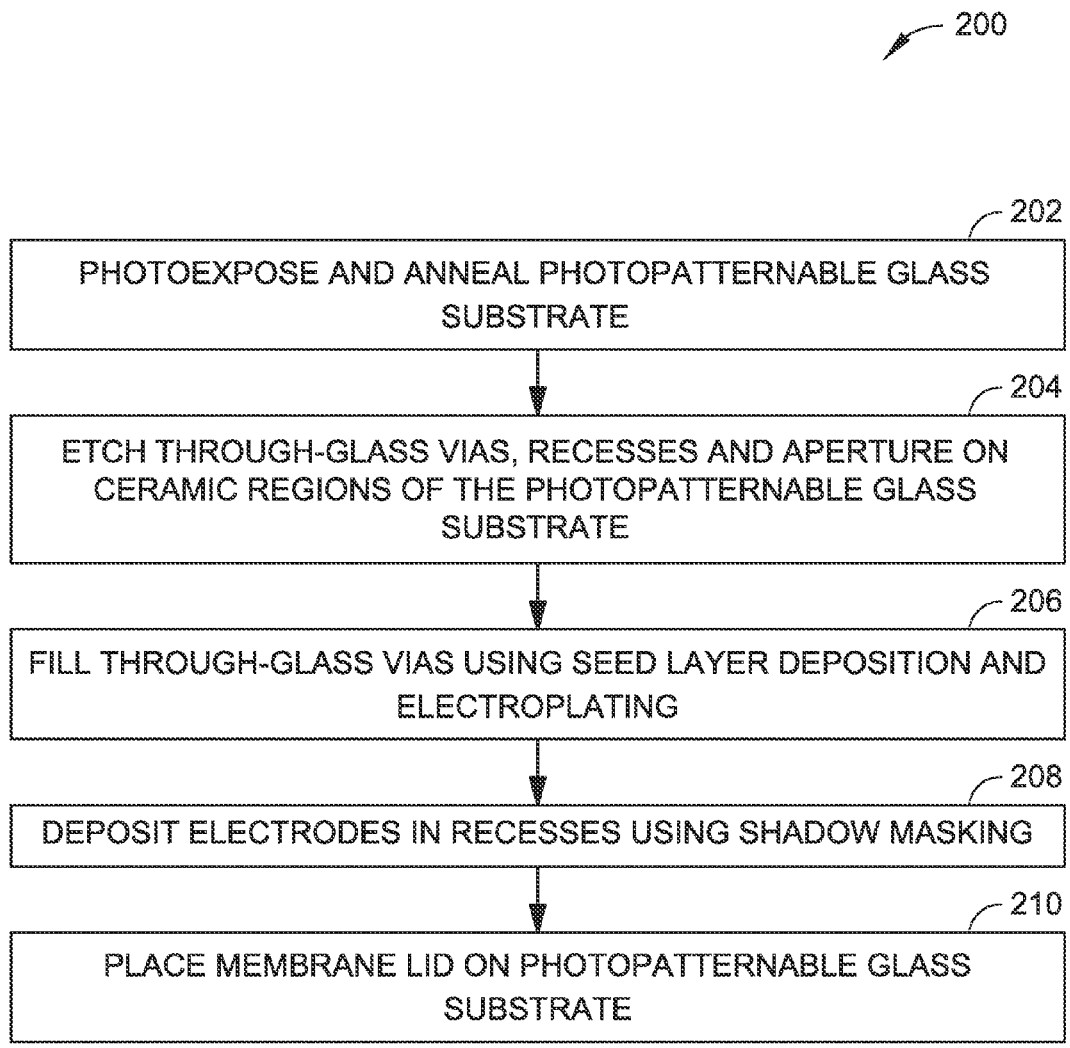
FIG. 4 is a flow diagram illustrating an example process for fabricating a micro electrochemical cell that includes a photopatternable glass substrate with through-glass vias, and a gas-permeable membrane lid, such as the micro electrochemical cell illustrated in FIGS. 1A through 1G.

FIG. 2 illustrates an example process 200 that employs techniques to fabricate micro electrochemical cells and electrochemical gas sensors, such as the micro electrochemical cell 100 shown in FIG. 1A and the electrochemical gas sensor 114 shown in FIG. 1B. FIGS. 3A through 3C illustrate sections 300 of an example micro electrochemical cell (such as the micro electrochemical cell 100 shown in FIGS. 1A through 1G).

As shown in FIG. 2, a cell body, an integrated circuit device, a connector assembly, and a cell (first) printed circuit board are assembled (Block 202). In implementations, assembling the cell body 117 can include using photoexposure, annealing, and etching a photodefinable glass 101 for forming at least one recess 101A and through-glass via 105. As the photoexposed portion of the photopatternable glass substrate 101 is exposed to light and baked and/or annealed, the glass converts to an etchable opaque ceramic after annealing. The ceramic regions of the photodefinable glass 101 can then be etched using a suitable etchant, such as hydrofluoric acid (HF). It is contemplated that other etchants may be utilized to etch the ceramic portion(s) of the photodefinable glass 101.

In an implementation, a recess 101A, a through-glass via 105, and other cavities can be formed by serial etching the ceramic regions of the exposed photopatternable glass substrate 101 with, for example, a less concentrated hydrofluoric acid (HF) solution than is used to etch glass. This ensures that only the ceramic portion is etched while the remaining glass portion is relatively unetched. In some implementations, blind etching can be used to form a through-glass via 105 and recess 101A in the photopatternable glass substrate 101. In implementations, different depths for a through-glass via 105 and/or recess 101A can be achieved by selectively masking the regions not to be etched, for example with etch-resistant blue tape or photoresist. Additionally, the photoexposure, anneal, and/or etch process can be performed multiple times to obtain the desired recess 101A and through-glass via 105 configuration(s).

In implementations, seed layer deposition and electroplating can be used to fill the through-glass vias. In implementations, backside seed layer deposition and electroplating can be utilized. In other implementations, front side seed layer deposition and electroplating can be used, followed by backside etching and/or backgrinding and polishing to reveal the plated seed through-glass via 105 and backside plating. In some implementations, side through-glass vias 105 can be formed, which may be hollow.

Assembling the cell body 117 can include forming an electrode in a recess 101A. In implementations, electrodes can be formed and/or defined using deposition processes and/or shadow-masking to prevent metallization on recess 101A sidewalls. Some examples of deposition processes can include physical vapor deposition (e.g., sputtering), electroplating, and/or chemical vapor deposition.

Further, assembling the integrated circuit device 115 can include coupling the cell body 117, an integrated circuit device 115, and/or a connector assembly 120 to a cell printed circuit board 118. In implementations, coupling the cell body 117, the integrated circuit device 115, and/or the connector assembly 120 to a cell printed circuit board 118 can include using an adhesive and/or a solder connection. In a specific embodiment, the cell body 117 can be coupled to the cell printed circuit board 118 using an adhesive 109, such as an epoxy and/or a glue. The integrated circuit device 115 and the connector assembly 120 can be coupled to the cell printed circuit board 118 by forming a solder ball array and reflowing the solder ball array. In some implementations, reflowing the solder ball array prior to dispensing an electrolyte 107 into the micro electrochemical cell 100 avoids exposing the electrolyte 107 to excessive heat, which potentially could destroy the electrolyte 107.

Next, an electrolyte is dispensed into the cell body (Block 204). In implementations, an electrolyte 107 can be dispensed into the cell body 117 and the recess 101A formed by etching the photopatternable glass 101. In some implementations, dispensing the electrolyte can include dispensing the electrolyte 107 prior to placement of the lid assembly 125 on the cell body 117. In other implementations, dispensing the electrolyte 107 can include dispensing the electrolyte 107 subsequent to placing the lid assembly 125 by using sealable holes and/or openings in the lid assembly 125 and/or lid 106. In a specific embodiment, dispensing the electrolyte 107 is performed subsequent to coupling an integrated circuit device 115 and/or a connector assembly 120 to a cell printed circuit board 118. This specific embodiment ensures that the dispensed electrolyte 107 is not exposed to excessive heat.

Then, the lid assembly is placed on the cell body (Block 206). In implementations, placing the lid assembly 125 can include affixing the lid assembly 125 to the cell body 117 with a critical gel adhesive 109 using an automated process, such as a pick-and-place technique. In embodiments, assembling the components in Block 202, dispensing the electrolyte 107 in Block 204, and/or placing the lid assembly 125 in Block 206 can be performed on a wafer level or a panel level.

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A micro electrochemical cell, comprising:
a substantially planar photopatternable glass substrate having a first side and a second side;
at least one recess formed in the first side of the photopatternable glass substrate, where the glass substrate and the recess form a cell body, and where the recess includes surface corrugation to provide electrode sensing surface area;
a plurality of through-glass vias formed in the photopatternable glass substrate, the through-glass vias extending from the first side of the photopatternable glass to the second side of the photopatternable glass;
a plurality of electrodes electrically connected to at least one through-glass via, where the at least one through-glass via forms an electrical connection from the plurality of the electrodes to the second side of the photopatternable glass;
at least one electrolyte disposed in the at least one recess;
a lid assembly disposed on the cell body and over the at least one recess, the lid assembly including a lid substrate including an aperture, the aperture including a gas permeable region.

2. The micro electrochemical cell in claim 1, wherein the photopatternable glass substrate is configured to be convertable to an etchable ceramic after exposure to light and an annealing process.

3. The micro electrochemical cell in claim 1, wherein the plurality of electrodes is disposed on the glass substrate.

4. The micro electrochemical cell in claim 1, wherein an at least one of the plurality of electrodes is disposed in at least one recess.

5. The micro electrochemical cell in claim 1, wherein the plurality of electrodes includes at least one of gold or platinum.

6. The micro electrochemical cell in claim 1, wherein the plurality of electrodes includes a counter electrode and at least one working electrode, with at least one working electrode disposed proximate to the aperture.

7. The micro electrochemical cell in claim 1, wherein the plurality of electrodes includes multiple working electrodes.

8. The micro electrochemical cell in claim 1, wherein the at least one electrolyte disposed in the at least one recess includes a gel electrolyte.

9. The micro electrochemical cell in claim 1, wherein the lid assembly includes at least one electrode.

10. The micro electrochemical cell in claim 1, wherein the lid assembly includes a porous membrane disposed between the aperture and the at least one recess.

11. The micro electrochemical cell in claim 1, further comprising a wicking layer disposed between the electrolyte and the electrodes.

12. A micro electrochemical system, comprising:
an application specific integrated circuit; and
a micro electrochemical cell electrically coupled to the application specific integrated circuit, the micro electrochemical cell including a substantially planar photopatternable glass substrate having a first side and a second side;
at least one recess formed in the first side of the photopatternable glass substrate, where the glass substrate and the recess form a cell body, and where the recess includes surface corrugation to provide electrode sensing surface area;
a plurality of through-glass vias formed in the photopatternable glass substrate, the through-glass vias extending from the first side of the photopatternable glass to the second side of the photopatternable glass;
a plurality of electrodes electrically connected to at least one through-glass via, where the at least one through-glass via forms an electrical connection from the plurality of the electrodes to the second side of the photopatternable glass;
at least one electrolyte disposed in the at least one recess;
a lid assembly disposed on the cell body and over the at least one recess, the lid assembly including
a lid substrate including an aperture, the aperture including a gas permeable region, and
a porous membrane disposed between the aperture and the at least one recess.

13. The micro electrochemical system in claim 12, wherein the micro electrochemical cell includes a recess configured for housing the application specific integrated circuit.

14. The micro electrochemical system in claim 12, further comprising a connector assembly.

15. The micro electrochemical system in claim 12, further comprising an electrical redistribution layer on the second side of photopatternable glass substrate.

* * * * *